United States Patent
Kang et al.

(10) Patent No.: US 11,690,520 B2
(45) Date of Patent: Jul. 4, 2023

(54) APPARATUS AND METHOD FOR MEASURING BIO-INFORMATION

(71) Applicant: SAMSUNG ELECTRONICS CO., LTD., Suwon-si (KR)

(72) Inventors: Jae Min Kang, Seoul (KR); Yong Joo Kwon, Yongin-si (KR); Youn Ho Kim, Hwaseong-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 987 days.

(21) Appl. No.: 16/393,432

(22) Filed: Apr. 24, 2019

(65) Prior Publication Data

US 2019/0387985 A1 Dec. 26, 2019

(30) Foreign Application Priority Data

Jun. 20, 2018 (KR) .................. 10-2018-0070927
Jan. 11, 2019 (KR) .................. 10-2019-0004099

(51) Int. Cl.
*A61B 5/021* (2006.01)
*A61B 5/00* (2006.01)

(52) U.S. Cl.
CPC ........ *A61B 5/02116* (2013.01); *A61B 5/0082* (2013.01); *A61B 5/7246* (2013.01)

(58) Field of Classification Search
None
See application file for complete search history.

(56) References Cited

U.S. PATENT DOCUMENTS

| | | | |
|---|---|---|---|
| 5,590,662 A * | 1/1997 | Hersh | A61B 5/0225 600/494 |
| 6,537,225 B1 | 3/2003 | Mills | |
| 6,873,865 B2 | 3/2005 | Steuer et al. | |
| 9,215,986 B2 | 12/2015 | Banet et al. | |
| 2003/0069507 A1* | 4/2003 | Nishibayashi | A61B 5/021 600/485 |

(Continued)

FOREIGN PATENT DOCUMENTS

| JP | 6285897 A | 2/2018 |
|---|---|---|
| KR | 10-2006-0081178 A | 7/2006 |

(Continued)

OTHER PUBLICATIONS

Communication dated Oct. 9, 2019, issued by the European Patent Office in counterpart European Application No. 19180854.2.

*Primary Examiner* — Jacqueline Cheng
*Assistant Examiner* — Jairo H Portillo
(74) *Attorney, Agent, or Firm* — Sughrue Mion, PLLC

(57) ABSTRACT

Provided are an apparatus and method for measuring bio-information. The apparatus for measuring bio-information includes: a pulse wave sensor configured to emit light of multiple wavelengths onto an object, and detect the light to obtain multi-wavelength pulse wave signals when the light is reflected or scattered from the object; and a processor configured to: obtain a conversion signal that indicates a contact pressure between the object and the pulse wave sensor, based on the multi-wavelength pulse wave signals, obtain an oscillometric envelope based on the multi-wavelength pulse wave signals and the conversion signal, and obtain bio-information based on the oscillometric envelope.

22 Claims, 14 Drawing Sheets

(56) References Cited

U.S. PATENT DOCUMENTS

| | | | |
|---|---|---|---|
| 2005/0209516 A1 | 9/2005 | Fraden | |
| 2006/0155196 A1* | 7/2006 | Ramsey | A61B 5/02141 600/490 |
| 2011/0144918 A1* | 6/2011 | Inoue | A61B 5/0225 702/179 |
| 2011/0218447 A1* | 9/2011 | Kinoshita | A61B 5/022 600/491 |
| 2012/0215118 A1* | 8/2012 | Chen | A61B 5/022 600/490 |
| 2013/0158969 A1* | 6/2013 | Donehoo | G09B 23/303 703/11 |
| 2014/0051941 A1 | 2/2014 | Messerschmidt | |
| 2015/0184029 A1 | 7/2015 | Grumbine et al. | |
| 2016/0038044 A1* | 2/2016 | Banerjee | A61B 5/7246 600/480 |
| 2016/0098955 A1 | 4/2016 | Huang et al. | |
| 2016/0113530 A1* | 4/2016 | Nagahiro | A61B 5/0082 600/407 |
| 2016/0120411 A1 | 5/2016 | Hadley et al. | |
| 2016/0278704 A1 | 9/2016 | Park et al. | |
| 2017/0071516 A1 | 3/2017 | Bhagat et al. | |
| 2017/0095168 A1 | 4/2017 | Kwon et al. | |
| 2017/0109495 A1 | 4/2017 | Xin | |
| 2017/0172430 A1 | 6/2017 | Zhao et al. | |
| 2017/0209052 A1 | 7/2017 | Nakamura | |
| 2017/0215749 A1* | 8/2017 | Zhuo | A61B 5/02055 |
| 2017/0337413 A1* | 11/2017 | Bhat | G06V 40/1318 |
| 2017/0367597 A1 | 12/2017 | Fortin | |
| 2018/0042486 A1* | 2/2018 | Yoshizawa | A61B 5/02416 |
| 2018/0085011 A1 | 3/2018 | Ma et al. | |
| 2018/0085012 A1 | 3/2018 | Wei et al. | |
| 2018/0192900 A1 | 7/2018 | Wei | |

FOREIGN PATENT DOCUMENTS

| | | |
|---|---|---|
| KR | 10-2017-0032877 A | 3/2017 |
| KR | 10-2017-0040034 A | 4/2017 |
| WO | 2015184029 A1 | 12/2015 |
| WO | 2016110781 A1 | 7/2016 |
| WO | 2016155138 A1 | 10/2016 |

* cited by examiner

APPARATUS AND METHOD FOR MEASURING BIO-INFORMATION

CROSS-REFERENCE TO RELATED APPLICATION(S)

This application claims priority from Korean Patent Application No. 10-2018-0070927, filed on Jun. 20, 2018, and Korean Patent Application No 10-2019-0004099, filed on Jan. 11, 2019, in the Korean Intellectual Property Office, the disclosures of which are incorporated herein by reference in their entireties.

BACKGROUND

1. Field

Example embodiments of the present disclosure relate to an apparatus and method for measuring bio-information, and more particularly to technology for measuring bio-information using an oscillometric method.

2. Description of the Related Art

As a method of measuring blood pressure in a non-invasive manner without causing pain to a human body, there is a cuff-based measurement method for measuring blood pressure using cuff pressure measurements and a cuffless measurement method for estimating blood pressure using pulse wave measurements without a cuff.

As the cuff-based measurement method for measuring blood pressure, there is a Korotkoff-sound method in which blood pressure is measured by using a cuff worn around an upper arm and hearing the sound of blood vessels through a stethoscope during inflation and deflation of the cuff; and an Oscillometric method in which blood pressure is measured at a point of a maximum pressure signal change by using a cuff worn around an upper arm and continuously measuring cuff pressure while the cuff is inflating and then gradually deflating.

As the cuffless measurement method for measuring blood pressure, there is a method of estimating blood pressure by calculating a Pulse Transit Time (PTT), and a Pulse Wave Analysis (PWA) method of estimating blood pressure by analyzing a pulse wave shape.

SUMMARY

According to an aspect of an example embodiment, there is provided an apparatus for measuring bio-information, the apparatus including: a pulse wave sensor configured to emit light of multiple wavelengths onto an object, and detect the light to obtain multi-wavelength pulse wave signals when the light is reflected or scattered from the object; and a processor configured to obtain a conversion signal that indicates a contact pressure between the object and the pulse wave sensor, based on the multi-wavelength pulse wave signals, obtain an oscillometric envelope based on the multi-wavelength pulse wave signals and the conversion signal, and obtain bio-information based on the oscillometric envelope.

The pulse wave sensor may include: one or more light sources configured to emit the light of the multiple wavelengths onto the object; and one or more detectors configured to detect the light of the multiple wavelengths when the light is reflected or scattered from the object.

In this case, the one or more detectors may be positioned at different distances from the one or more light sources.

Further, each of the one or more detectors may include at least one of a light emitting diode (LED), a laser diode, and a fluorescent body.

The multiple wavelengths may include two or more of an infrared wavelength, a red wavelength, a green wavelength, and a blue wavelength.

The processor may be further configured to obtain a differential signal between the multi-wavelength pulse wave signals, and obtain the conversion signal based on the differential signal.

The processor may be further configured to obtain the conversion signal corresponding to the differential signal, based on a correlation model that uses a correlation between an intensity of the differential signal at each measurement time and an actual contact pressure.

The multi-wavelength pulse wave signals may include a pulse wave signal having a blue wavelength, and the processor may be further configured to obtain the differential signal by subtracting the pulse wave signal having the blue wavelength from the pulse wave signals having wavelengths other than the blue wavelength.

The multi-wavelength pulse wave signals may include a pulse wave signal having a blue wavelength, a pulse wave signal having a green wavelength, and a pulse wave signal having a red wavelength, and the processor may be further configured to obtain a first differential signal by subtracting the pulse wave signal having the blue wavelength from the pulse wave signal having the green wavelength, a second differential signal obtained by subtracting the pulse wave signal having the blue wavelength from the pulse wave signal of the red wavelength, and obtain the conversion signal based on a ratio between the first differential signal and the second differential signal.

The processor may be further configured to: select one or more pulse wave signals from the multi-wavelength pulse wave signals based on at least one of a maximum amplitude value and an average amplitude value of each of the multi-wavelength pulse wave signals, and a difference between the maximum amplitude value and a minimum amplitude value of each of the multi-wavelength pulse wave signals; and obtain the oscillometric envelope based on the selected one or more pulse wave signals and the conversion signal.

The processor may be further configured to: select, from the multi-wavelength pulse wave signals, a first pulse wave signal and a second pulse wave signal that has a longer wavelength that the first pulse wave signal; obtain a differential signal by subtracting the first pulse wave signal from the second pulse wave signal; and obtain the oscillometric envelope based on the differential signal and the conversion signal.

The processor may be further configured to: select a plurality of pulse wave signals from the multi-wavelength pulse wave signals; obtain the oscillometric envelope using each of the selected pulse wave signals and the conversion signal; and obtain a combined oscillometric envelope by combining the oscillometric envelope obtained from each of the selected pulse wave signals.

The processor may be further configured to: select pulse wave signals from the multi-wavelength pulse wave signals; extract a peak-to-peak amplitude at each measurement time of the selected pulse wave signals; and obtain the oscillometric envelope by plotting the extracted peak-to-peak amplitude with respect to a value of the conversion signal corresponding to the each measurement time.

The processor may be further configured to extract as features, one or more of an amplitude value or a contact pressure value of a maximum peak of the oscillometric envelope, and contact pressure values located having a predetermined ratio to the contact pressure value of the maximum peak.

The bio-information may include one or more of blood pressure, vascular age, arterial stiffness, aortic pressure waveform, vascular compliance, stress index, and degree of fatigue.

The apparatus for measuring bio-information may further include an output interface configured to output a processing result of the processor.

The apparatus may further include an output interface configured to, based on receiving a request form measuring bio-information, output information on a reference contact pressure to be applied by a user to the pulse wave sensor.

The apparatus may further include an output interface configured to output information on a measured contact pressure, applied by a user to the pulse wave sensor, based on the conversion signal.

According to an aspect of another example embodiment, there is provided a method of measuring bio-information, including: emitting, by a pulse wave sensor, light of multiple wavelengths onto an object; detecting, by the pulse wave sensor, the light to obtain multi-wavelength pulse wave signals when the light is reflected or scattered from the object; obtaining a conversion signal that indicates a contact pressure between the object and the pulse wave sensor, based on the multi-wavelength pulse wave signals; obtaining an oscillometric envelope based on the multi-wavelength pulse wave signals and the conversion signal; and obtaining bio-information based on the oscillometric envelope.

The obtaining the conversion signal may include obtaining a differential signal between the multi-wavelength pulse wave signals, and obtaining the conversion signal based on the differential signal.

The obtaining the conversion signal may include, based on the multi-wavelength pulse wave signals including a pulse wave signal having a blue wavelength, obtaining the differential signal by subtracting the pulse wave signal having the blue wavelength from the pulse wave signals having wavelengths other than the blue wavelength.

The obtaining the conversion signal may include: based on the multi-wavelength pulse wave signals including a pulse wave signal having a blue wavelength, a pulse wave signal having a green wavelength, and a pulse wave signal having a red wavelength, obtaining a first differential signal by subtracting the pulse wave signal having the blue wavelength from the pulse wave signal having the green wavelength, and a second differential signal by subtracting the pulse wave signal having the blue wavelength from the pulse wave signal of the red wavelength; and obtaining the conversion signal based on a ratio between the first differential signal and the second differential signal.

The obtaining the oscillometric envelope may include: selecting one or more pulse wave signals from the multi-wavelength pulse wave signals based on at least one of a maximum amplitude value and an average amplitude value of each of the multi-wavelength pulse wave signals, and a difference between the maximum amplitude value and a minimum amplitude value of each of the multi-wavelength pulse wave signals; and obtaining the oscillometric envelope based on the selected one or more pulse wave signals and the conversion signal.

The obtaining the oscillometric envelope may include: selecting, from the multi-wavelength pulse wave signals, a first pulse wave signal and a second pulse wave signal that has a longer wavelength than the first pulse wave signal; obtaining a differential signal by subtracting the first pulse wave signal from the second pulse wave signal; and obtaining the oscillometric envelope based on the differential signal and the conversion signal.

The obtaining the oscillometric envelope may include: selecting a plurality of pulse wave signals from the multi-wavelength pulse wave signals; obtaining the oscillometric envelope using each of the selected pulse wave signals and the conversion signal; and obtaining a combined oscillometric envelope by combining the oscillometric envelope obtained from each of the selected pulse wave signals.

The obtaining the bio-information may include extracting, as features, one or more of an amplitude value or a contact pressure value of a maximum peak of the oscillometric envelope, contact pressure values located having a predetermined ratio to the contact pressure value of the maximum peak.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
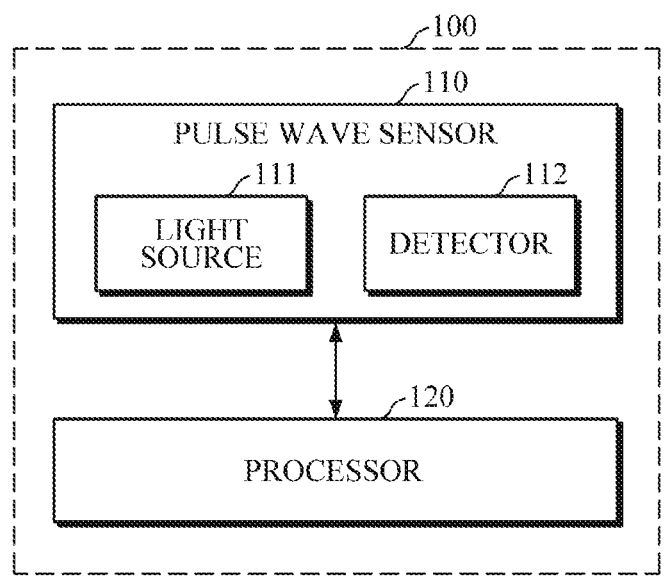
FIG. 1 is a block diagram illustrating an apparatus for measuring bio-information according to an embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of an apparatus and method for measuring bio-information will be described in detail with reference to the accompanying drawings.

FIG. 1 is a block diagram illustrating an apparatus for measuring bio-information according to an embodiment of the present disclosure.

Referring to FIG. 1, the bio-information measuring apparatus 100 includes a pulse wave sensor 110 and a processor 120.

The pulse wave sensor 110 may include a light source 11 and a detector 112 to measure a photoplethysmography (PPG) signal (hereinafter referred to as a pulse wave signal) from an object. In the embodiment, the pulse wave sensor 110 may measure pulse wave signals having multiple wavelengths from an object. In particular, the multiple wavelengths may include an infrared wavelength, a red wavelength, a green wavelength, a blue wavelength, and the like.

The light source 111 may emit light onto an object, and the detector 112 may detect the light when the light emitted from the light source 111 is scattered, deflected, or reflected from a body tissue such as the surface of skin or blood vessels of the object.

The light source 111 may include a light emitting diode (LED), a laser diode (LD), a fluorescent body, and the like. One or more light sources 111 may be provided to emit light of multiple wavelengths onto an object for detection of multi-wavelength pulse wave signals. For example, the pulse wave sensor 110 may include a plurality of light sources 111 which may emit light of different wavelengths, and may be positioned at different distances from the detector 112, or may include a plurality of detectors 112 positioned at different distances from the light source 111. In another example, the pulse wave sensor 110 may include a single light source 111 which sequentially emits light of different wavelengths under the control of the processor 120, and a single light source 111 which emits light in a wide wavelength range including a range of multiple wavelengths desired to be detected.

The detector 112 may include one or more photo diodes, photo transistors (PTr), image sensors (e.g., CMOS image sensor), and the like. The detector 112 may be provided to correspond to each of the plurality of light sources 111 to detect light of multiple wavelengths. Alternatively, a plurality of detectors 112 may be formed to respond to light of different wavelengths, to detect multi-wavelength light emitted by the single light source 111.

Upon receiving a request for measuring bio-information, the processor 120 may refer to reference information to provide guidance information on an intensity of a reference contact pressure to be applied by a user. Further, the processor 120 may drive the pulse wave sensor 110 in response to the request for measuring bio-information. Based on predetermined light source driving conditions, the processor 120 may sequentially drive the light sources 111 to emit light of multiple wavelengths. In particular, the light source driving conditions may include a light intensity, a pulse duration, and the like of each of the light sources 111.

Upon receiving a multi-wavelength pulse wave signal detected by the pulse wave sensor 110 at a specific time, the processor 120 may analyze the received multi-wavelength pulse wave signal, and may obtain a conversion signal that indicates contact pressure between the object and the pulse wave sensor 110.

In addition, the processor 120 may measure bio-information based on the received multi-wavelength pulse wave signal and/or the conversion signal. In particular, the bio-information may include heart rate, systolic blood pressure, diastolic blood pressure, vascular age, arterial stiffness, aortic pressure waveform, vascular compliance, stress index, degree of fatigue, and the like, but is not limited thereto. For example, the processor 120 may obtain an oscillometric envelope based on the multi-wavelength pulse wave signal and the conversion signal, and may measure bio-information by using the obtained oscillometric envelope.

Figure 2:
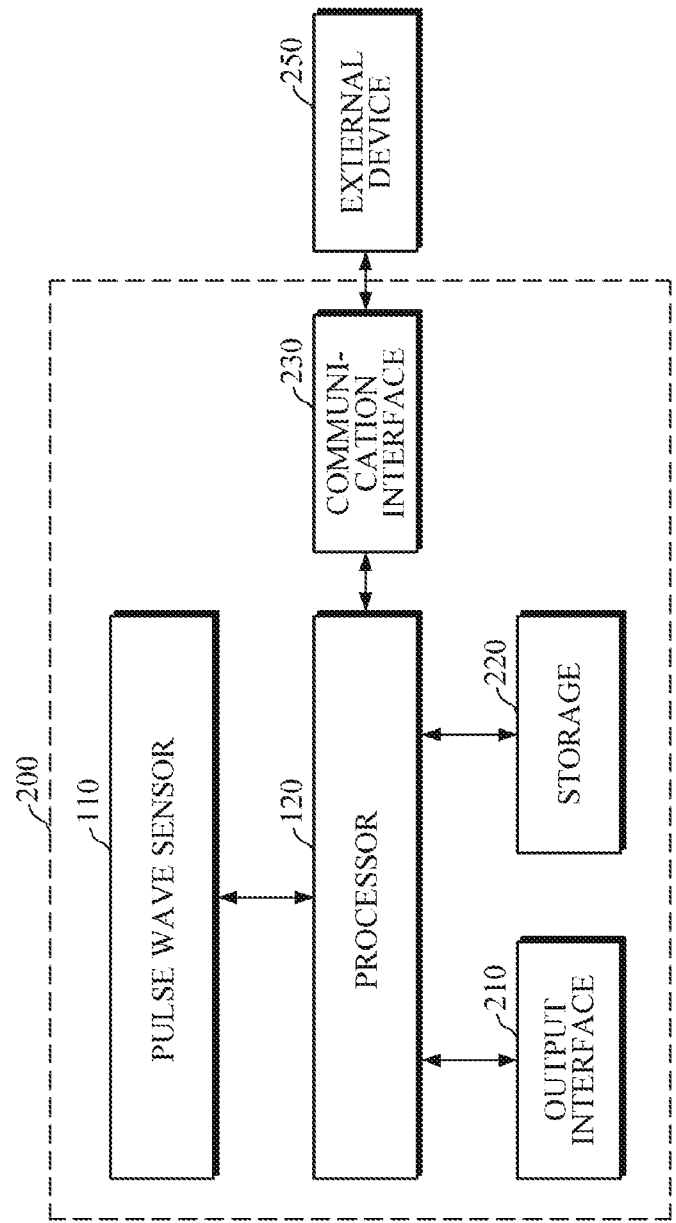
FIG. 2 is a block diagram illustrating an apparatus for measuring bio-information according to another embodiment of the present disclosure.

FIG. 2 is a block diagram illustrating an apparatus for measuring bio-information according to another embodiment of the present disclosure.

Referring to FIG. 2, the bio-information measuring apparatus 200 may include a pulse wave sensor 110, a processor 120, an output interface 210, a storage 220, and a communication interface 230. The pulse wave sensor 110 and the processor 120 are described above with reference to FIG. 1, such that the following description will be made based on other parts.

The output interface 210 may output the multi-wavelength pulse wave signal detected by the pulse wave sensor 110, or a processing result (e.g., a measurement result of bio-information) of the processor 120. In this case, the output interface 210 may visually provide various types of information to a user through a display. Alternatively, the output interface 210 may provide various types of information to a user in a non-visual manner through voice, vibrations, tactile sensation, and the like by using a speaker, a haptic motor, a vibrator, and the like. For example, if a measured blood pressure value falls outside a predetermined normal range, the output interface 210 may output warning information by highlighting an abnormal value in red, or may further output warning information through vibrations and tactile sensation using a haptic module.

Further, upon receiving a request for measuring bio-information, the output interface 210 may output guidance information on contact pressure to be applied by a user to the pulse wave sensor 110 under the control of the processor 120. The guidance information may include an intensity of contact pressure applied by an object to the pulse wave sensor 110 while the pulse wave sensor 110 detects a pulse wave signal, and/or information on an actual contact pressure extracted by the processor 120.

For example, upon receiving the request for measuring bio-information, the output interface 210 may output a graph of time versus contact pressure during a predetermined period of time on a display under the control of the processor 120, and may output an identification mark indicating a reference contact pressure value required to be applied by a user at each measurement point and/or a range of reference contact pressure values on the graph. For example, the identification mark may include a line formed by connecting points corresponding to the reference contact pressure values of each measurement point, a line formed by connecting maximum values in the range of reference contact pressure values, or a line formed by connecting minimum values in the range of reference contact pressure values.

Further, once the processor 120 obtains a conversion signal, which indicates contact pressure, by using the multi-wavelength pulse wave signal, and obtains a contact pressure value which corresponds to an actual contact pressure applied by a user to the pulse wave sensor 110 at each measurement time, the output interface 210 may output the obtained contact pressure value at each measurement time on a graph. By comparing a reference contact pressure with the contact pressure obtained based on the conversion signal, the processor 120 may generate warning information to prompt a user to change his/her force or contact pressure exerted to the bio-information measuring apparatus 200, and the output interface 210 may visually output the generated warning information or may output the warning information through voice, vibrations, and the like.

The storage 220 may store various types of reference information or a processing result of the pulse wave sensor 110 and/or the processor 120. Various types of reference information may include user information, such as a user's age, sex, health condition, and the like, a reference contact pressure value, a range of reference contact pressure values, reference information for calibration, such as cuff pressure or cuff blood pressure, guidance information on a measurement state described above, information required for measuring bio-information such as a bio-information measurement model and the like.

In particular, the storage 220 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

In the embodiment, upon receiving a request for calibration from a user, or at predetermined calibration intervals, the processor 120 may calibrate a bio-information measurement model or a bio-information measurement value. Alternatively, upon measuring bio-information, the processor 120 may determine whether to perform calibration based on a measurement result of bio-information.

For example, in the case in which a bio-information measurement value falls outside a predetermined normal range, the processor 120 may determine to perform calibration. Alternatively, in the case in which the bio-information measurement value falls outside the normal range, and a total number of times the bio-information measurement value falls outside the normal range during a predetermined period of time is greater than or equal to a threshold value, the processor 120 may determine to perform calibration. In addition, in the case in which a bio-information measurement value falls outside the normal range, and a number of times previous bio-information measurement values, including the value, continuously fall outside a normal range is greater than or equal to a threshold value, the processor 120 may determine to perform calibration. However, this is merely an example, and the determination is not limited thereto. The processor 120 may also set criteria for determining calibration by considering various conditions, such as information on whether an object and/or a measurement state has been changed, information on whether a user's health condition has been changed, and the like.

Upon determining to perform calibration, the processor 120 may obtain reference information for calibration from the storage 220, and may calibrate a bio-information measurement value or a bio-information measurement model. The reference information for calibration may include an actual bio-information measurement value (e.g., cuff pressure), an offset value, and the like, but is not limited thereto.

The processor 120 may control the communication interface 230 according to predetermined criteria to receive the reference information for calibration from an external device 250. In particular, the predetermined criteria may include a specific interval, a user's health condition, a state of an object, and the aforementioned criteria for determining calibration, and the like. For example, in the case in which a user's health condition is changed, and/or at specific intervals, the processor 120 may control the communication interface 230. Alternatively, in the case in which calibration has been performed a predetermined number of times or more, the processor 120 may determine that there is a change in the reference information, such as a reference blood pressure and the like, and may control the communication interface 230 to obtain new reference information.

The communication interface 230 may communicate with various external devices 250 under the control of the processor 120. The external device 250 may include an information processing device, such as a smartphone, a tablet PC, a desktop computer, and the like. Further, the external device 250 may include an apparatus for measuring bio-information, such as a cuff-type blood pressure measuring apparatus, which may measure bio-information more accurately. However, the external device 250 is not limed thereto.

The communication interface 230 may communicate with the external device 250 using communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The communication interface 230 may receive, from the external device 250, reference information for calibrating a bio-information measurement value under the control of the processor 120, and may store the received reference information in the storage 220.

Figure 3:
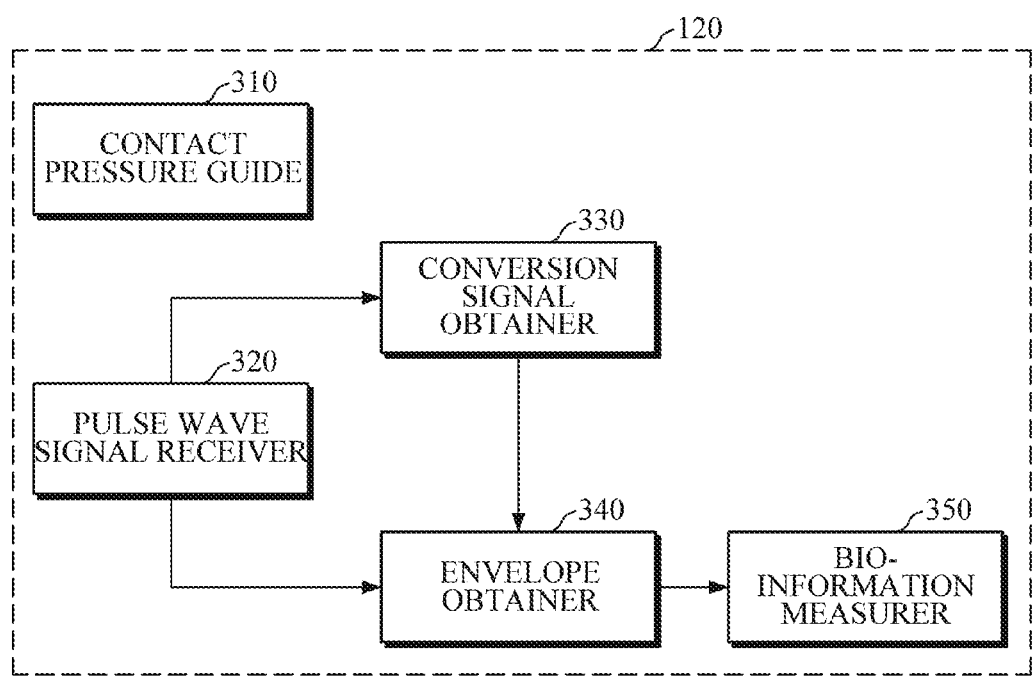
FIG. 3 is a block diagram illustrating a configuration of a processor according to an embodiment of the present disclosure.
Figure 4:
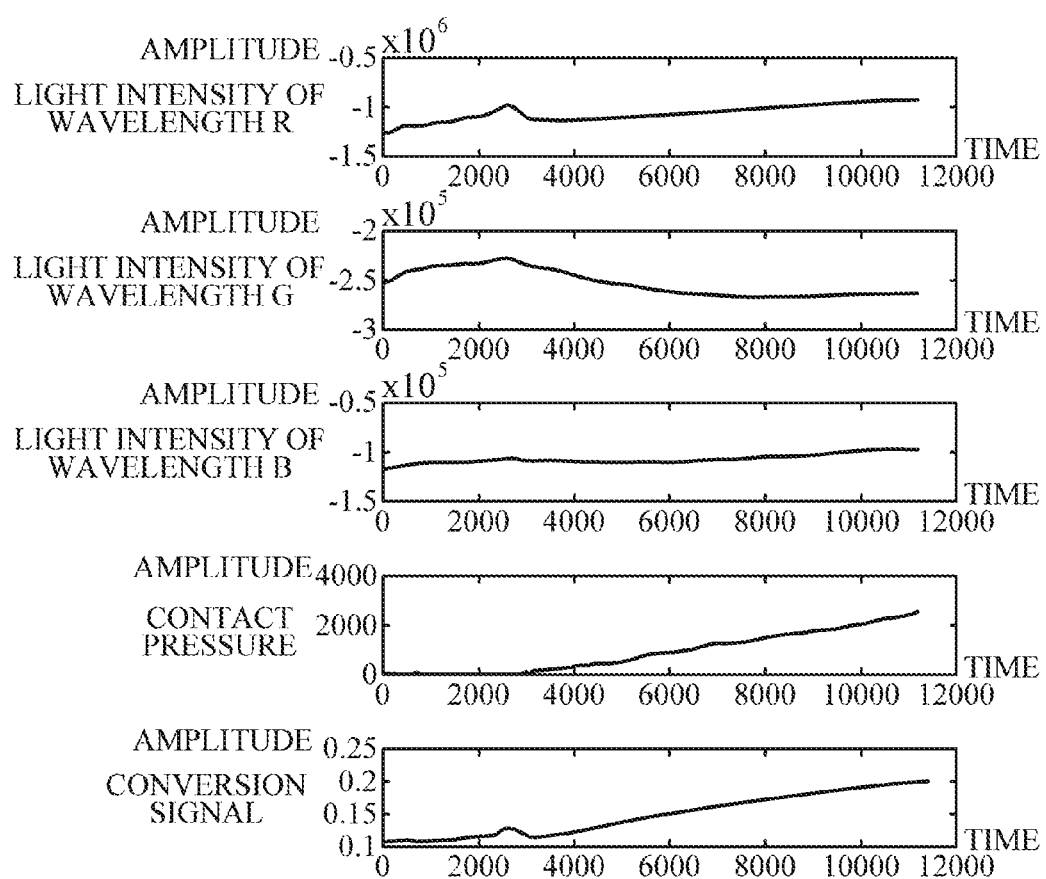
FIG. 4 is a diagram explaining a correlation between a multi-wavelength pulse wave signal, a conversion signal, and contact pressure.
Figure 5A:
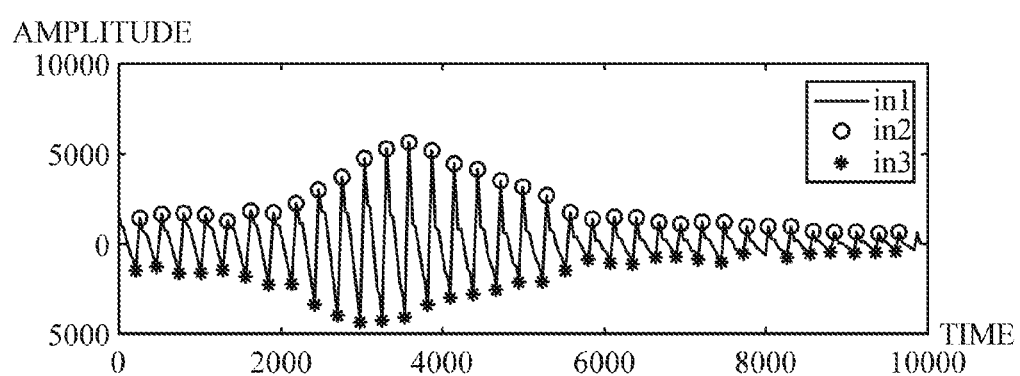
FIGS. 5A and 5B are diagrams explaining an example of measuring blood pressure using an oscillometric method.
Figure 5B:
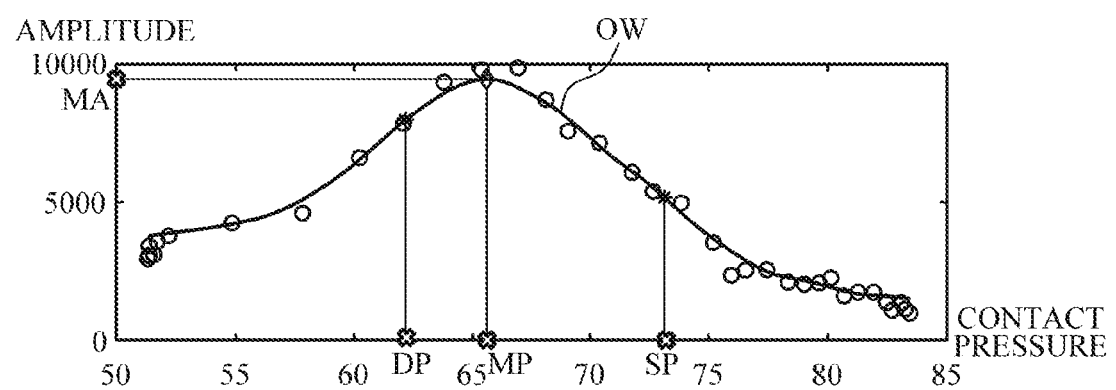
Figure 6A:
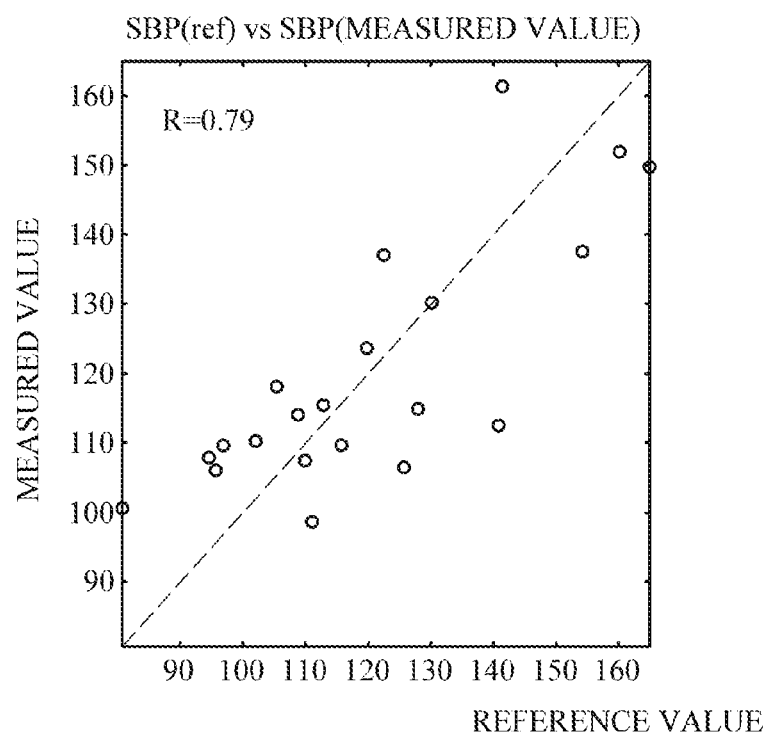
FIGS. 6A to 6C are diagrams explaining a correlation between a measured blood pressure value and an actual blood pressure value.
Figure 6B:
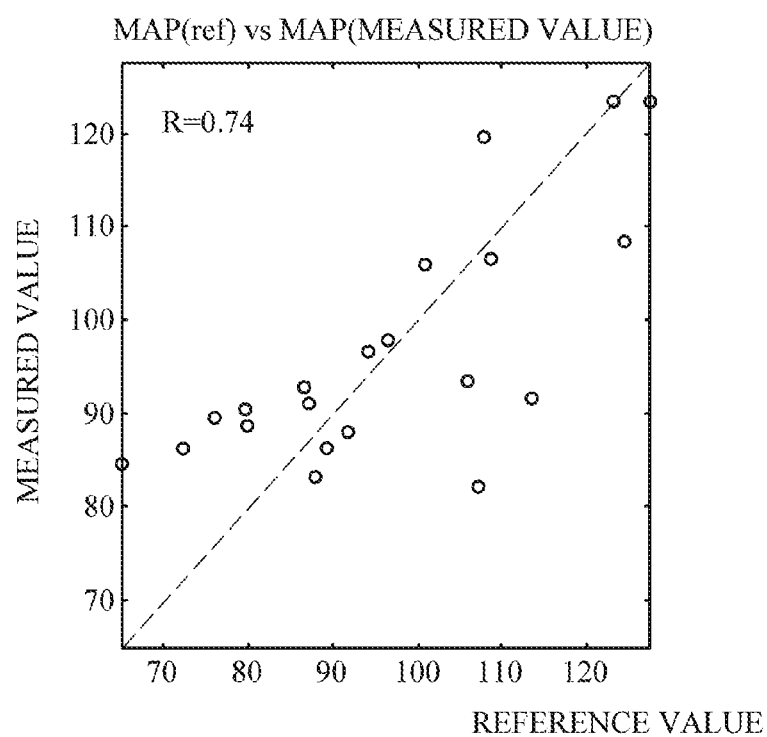
Figure 6C:
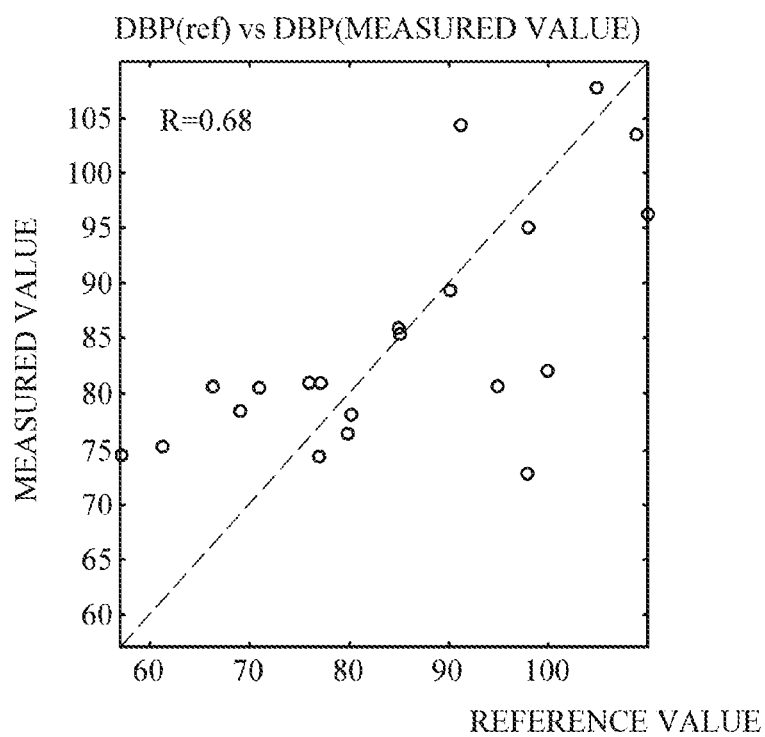

FIG. 3 is a block diagram illustrating a configuration of a processor according to an embodiment of the present disclosure. FIG. 4 is a diagram explaining a correlation between a multi-wavelength pulse wave signal, a conversion signal, and contact pressure. FIGS. 5A and 5B are diagrams explaining an example of measuring blood pressure using an oscillometric method. FIGS. 6A to 6C are diagrams explaining a correlation between a measured blood pressure value and an actual blood pressure value.

Referring to FIG. 3, the processor 120 includes a contact pressure guide 310, a pulse wave signal receiver 320, a conversion signal obtainer 330, an envelope obtainer 340, and a bio-information measurer 340.

Upon receiving a request for measuring bio-information, the contact pressure guide 310 may retrieve reference information from the storage 220 to provide a user with a reference contact pressure to be applied by the user to the pulse wave sensor 110 during a measurement time through the output interface 210. The reference contact pressure may be preset for each user based on a user's sex, age, a body part of the user to be contacted with the pulse wave sensor, a state of a body composition or portion to be examined, a health condition, a bio-information measurement history, and the like.

For example, the contact pressure guide 310 may output a graph including an identification mark, which indicates a reference contact pressure, through the output interface 210. The identification mark may indicate a reference contact pressure value that is recommended to be applied and to be compared with a measured contact pressure value while a user is in contact with the pulse wave sensor 110, a range of reference contact pressure values (e.g., a minimum value, a maximum value, and/or a mean value of the reference contact pressure values). For example, the output interface 210 may output a predetermined mark (e.g., a shape such as a circle, a square, an arrow, etc.) at a point on the graph which corresponds to the reference contact pressure value of each measurement time. Alternatively, the output interface 21 may display lines, each of which is formed by connecting minimum values, maximum values, mean values, and the like, so that a range of reference contact pressure values may be identified easily at each measurement time. However, the output interface 210 is not limited thereto, and may visually display the identification mark in various shapes or through voice and the like.

In addition, once the conversion signal obtainer 330 obtains a conversion signal which indicates contact pressure at each measurement time, the contact pressure guide 310 may output on a display contact pressure, obtained based on the conversion signal, through the output interface 210.

The pulse wave signal receiver 320 may receive a multi-wavelength pulse wave signal detected by the pulse wave sensor 110, and may transmit the received multi-wavelength pulse wave signal to the conversion signal obtainer 330 and the envelope obtainer 340. The pulse wave signal receiver 320 may be electrically connected to the pulse wave sensor 110.

Upon receiving the multi-wavelength pulse wave signal, the pulse wave signal receiver 310 may remove noise from the multi-wavelength pulse wave signal by filtering or may normalize the pulse wave signal, if necessary, before transmitting the pulse wave signal to the conversion signal obtainer 330 and the envelope obtainer 340. In this case, the pulse wave signal receiver 310 may obtain a pulse wave direct current (DC) signal of each wavelength by passing each pulse wave signal through a low-pass filter.

Upon receiving the multi-wavelength pulse wave signal at a specific point from the pulse wave sensor 110, the conversion signal obtainer 330 may obtain a conversion signal which indicates contact pressure between the object and the pulse wave sensor 110 at the specific point.

For example, the conversion signal obtainer 330 may generate differential signals by subtracting a pulse wave DC signal having a blue wavelength B, which is obtained at a specific point, from pulse wave DC signals having an infrared wavelength IR, a red wavelength R, and a green wavelength G, and may extract contact pressure at the specific time by combining the generated differential signals.

For example, as represented by the following Equation 1, the conversion signal obtainer 330 may calculate a first differential signal by subtracting the pulse wave signal having the blue wavelength from the pulse wave signal having the green wavelength, a second differential signal by subtracting the pulse wave signal having the blue wavelength from the pulse wave signal having the red wavelength, and calculate a ratio between the first differential signal and the second differential signal. Based on the calculated ratio, the conversion signal obtainer 330 may obtain a conversion signal which indicates contact pressure at each measurement time. Alternatively, the conversion signal obtainer 330 may obtain contact pressure by inputting the calculated ratio into a predefined correlation model. By using the obtained conversion signal, the conversion signal obtainer 330 may obtain contact pressure at each measurement time. In particular, the correlation model may use a functional algorithm or a patching table, but is not limited thereto.

$$Dr=(Sg-Sb)/(Sr-Sb)$$

$$CP=a \times Dr+b \quad \text{[Equation 1]}$$

Herein, Sg may denote an amplitude of the pulse wave DC signal having the green wavelength G, Sb may denote an amplitude of the pulse wave DC signal having the blue wavelength B, and Sr may denote an amplitude of the pulse wave DC signal having the red wavelength R. When there is a reference pulse signal having a reference wavelength, Dr may denote a ratio between differential signals, which may be represented as, for example, a ratio of am amplitude difference (e.g., Sg−Sb) between a first pulse signal of a first wavelength (e.g., Sg having the green wavelength G) the and the reference pulse signal (e.g., Sb having the blue wavelength B), to an amplitude difference (e.g., Sr−Sb) between a second pulse signal of a second wavelength (e.g., Sr having the red wavelength R) and the reference pulse signal (e.g., Sb having the blue wavelength) a and b may denote predetermined constants which define a correlation between a ratio of differential signals and contact pressure.

FIG. 4 is a diagram explaining a correlation between the pulse wave signal of each wavelength and a conversion signal, and contact pressure. For comparison of an actual contact pressure applied by a user with the conversion signal obtained in the embodiment of the present disclosure, FIG. 4 illustrates pulse wave signals having red, green, and blue wavelengths R, G, and B which are measured from an object during a predetermined period of time by a device including a contact pressure sensor, an actual contact pressure measured by the contact pressure sensor, and a conversion signal which indicates contact pressure and is obtained by the above method using the pulse wave signals having multiple wavelengths R, G, and B.

As illustrated in FIG. 4, there is a high correlation between the contact pressure of the conversion signal, obtained using the multi-wavelength pulse wave signals, and the actual contact pressure measured using the contact pressure sensor. Accordingly, in the embodiment of the present disclosure, a contact pressure value, which is similar to the actual contact pressure value of a user, may be obtained based on the conversion signal using the multi-wavelength pulse wave signals, such that bio-information may be measured accurately. Further, there is no need for a separate contact pressure sensor (e.g., a force sensor or an area sensor) such that the apparatus may be manufactured in a compact size.

The envelope obtainer 340 may obtain an oscillometric envelope by using the multi-wavelength pulse wave signals and the conversion signal. The envelope obtainer 340 may select one or more pulse wave signals from the multi-wavelength pulse wave signals according to predetermined criteria, and may obtain the oscillometric envelope by using the selected pulse wave signals and the conversion signal. In particular, the predetermined criteria may include at least one of a maximum amplitude value and an average amplitude value of each of the multi-wavelength pulse wave signals, and a difference between a maximum amplitude value and a minimum amplitude value. However, the envelope obtainer 340 is not limited thereto, and may select a pulse wave signal having a predetermined specific wavelength from among the multi-wavelength pulse wave signals.

For example, the envelope obtainer 340 may select a pulse wave signal having the largest difference between a maximum amplitude value and a minimum amplitude value. Upon selecting any one pulse wave signal, the envelope obtainer 340 may extract a peak-to-peak amplitude at each measurement time of the selected pulse wave signal, and may obtain an oscillometric envelope, which represents contact pressure versus pulse wave signal amplitude at each measurement time, by plotting the peak-to-peak amplitude with respect to a value of the conversion signal corresponding to each measurement time (i.e., a contact pressure value).

Referring to FIG. 5A, the envelope obtainer 340 may extract a peak-to-peak amplitude by subtracting an amplitude value in3 of a negative (−) point from an amplitude value in2 of a positive (+) point of a waveform envelope in1 at each measurement time of the selected pulse wave signal. Then, as illustrated in FIG. 5B, the envelope obtainer 340 may obtain an oscillometric envelope OW by plotting the peak-to-peak amplitude at each measurement time with respect to a contact pressure value of the conversion signal.

In another example, the envelope obtainer 340 may select two or more pulse wave signals according to predetermined criteria. For example, the envelope obtainer 340 may select a pulse wave signal having a relatively long wavelength (e.g., an infrared wavelength) and a wavelength having a relatively short wavelength (e.g., a green wavelength), and may subtract the pulse wave signal having a short wavelength from the pulse wave signal having a relatively long wavelength, to obtain an oscillometric envelope by using a differential signal, as described above. In particular, the envelope obtainer 340 may perform secondary differentiation on each of the pulse wave signals, and may obtain a differential signal by subtracting a differentiated signal having a short wavelength from a differentiated signal having a long wavelength.

In yet another example, the envelope obtainer 340 may obtain the oscillometric envelope by using at least some of the multi-wavelength pulse wave signals or all the multi-wavelength pulse wave signals. For example, the envelope obtainer 340 may obtain each oscillometric envelope by using each pulse wave signal and the conversion signal, and may obtain one combined oscillometric envelope by inputting the obtained each oscillometric envelope into a preset linear function or a combination model as represented by the following Equation 2. In this case, each oscillometric envelope may be obtained as described above.

$$f_{total} = c_1 f_1 + c_2 f_2 + c_3 f_3 \quad \text{[Equation 2]}$$

Herein, $f_1$, $f_2$, and $f_3$ each denotes the oscillometric envelope; $c_1$, $c_2$, and $c_3$ denote coefficients for each oscillometric envelope; and $f_{total}$ denotes the combined oscillometric envelope, in which the coefficients $c_1$, $c_2$, and $c_3$ for each oscillometric envelope may be pre-calculated through preprocessing based on a type of an apparatus to be applied, a portion to be examined, the size of an apparatus, a light intensity of each light emitter, a wavelength band, a user's health condition, and the like, but the coefficients are not limited thereto.

In an embodiment of the present disclosure, the envelope obtainer 340 may be provided outside the processor 120, and may be embodied as an envelope detector to capture the amplitudes of the multi-wavelength pulse wave signals and to provide the envelopes of the multi-wavelength pulse wave signals as an output. The envelope detector may include a rectifier that charges a capacitor to a peak voltage of the multi-wavelength pulse wave signals, by using a diode.

A bio-information measurer 350 may measure bio-information by using the oscillometric envelope obtained by the envelope obtainer 340. The bio-information measurer 350 may extract one or more features from the oscillometric envelope, and may measure bio-information by using the extracted features.

Referring to FIG. 5B, the bio-information measurer 350 may extract, as the feature values, an amplitude value MA or a contact pressure value MP of a maximum peak of the oscillometric envelope OW, and contact pressure values SP and DP located to the left and right of the contact pressure value MP of the maximum peak and having a predetermined ratio (e.g., 0.5 to 0.7) to the contact pressure value MP. The bio-information measurer 350 may measure bio-information by using the extracted feature values.

For example, when measuring blood pressure, the bio-information measurer 350 may calculate, as mean arterial pressure (MAP), the contact pressure value MP of the maximum peak of the oscillometric envelope OW. Further, the bio-information measurer 350 may calculate, as systolic blood pressure (SBP), the contact pressure value SP located to the right of the contact pressure value MP of the maximum peak in a predetermined ratio to the contact pressure value MP; and may calculate, as diastolic blood pressure (DBP), the contact pressure value DP located to the left of the contact pressure value MP of the maximum peak in a predetermined ratio to the contact pressure value MP.

Alternatively, upon extracting one or more features from the oscillometric envelope, the bio-information measurer 350 may measure bio-information by using a predefined measurement model as represented by the following Equation 3.

$$y = ax + b \quad \text{[Equation 3]}$$

Herein, y denotes a bio-information value to be obtained, for example, such as diastolic blood pressure (DBP), systolic blood pressure (SBP), mean arterial pressure (MAP), and the like; x denotes the extracted feature value; and a and b denote pre-calculated values obtained through preprocessing, and may be defined differently according to the types of bio-information to be obtained, e.g., diastolic blood pressure (DBP), systolic blood pressure (SBP), mean arterial pressure (MAP). However, the equation is not limited thereto, and may be predefined in the form a mapping table in which blood pressure values are mapped to the feature values.

FIGS. 6A to 6C are graphs showing a correlation between measurement values of systolic blood pressure (SBP), diastolic blood pressure (DBP), and mean arterial pressure (MAP) measured by the bio-information measurer 350 using an oscillometric envelope, and reference values of systolic blood pressure (SBP), diastolic blood pressure (DBP), and mean arterial pressure (MAP) measured by a blood pressure measuring apparatus such as a cuff sphygmomanometer. In the embodiment illustrated herein, bio-information may be measured accurately even without using a sensor for measuring an actual contact pressure.

Figure 7:
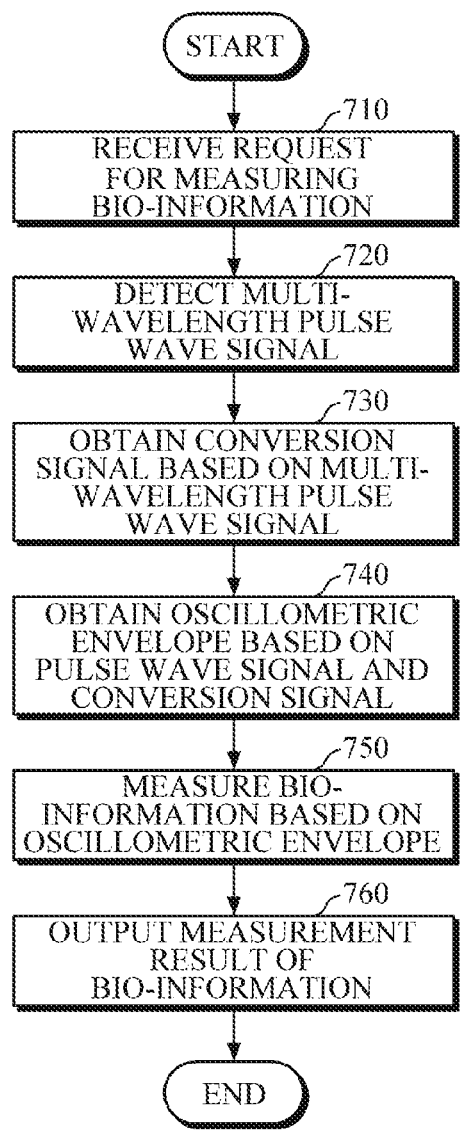
FIG. 7 is a flowchart illustrating a method of measuring bio-information according to an embodiment of the present disclosure.

FIG. 7 is a flowchart illustrating a method of measuring bio-information according to an embodiment of the present disclosure.

The method of FIG. 7 may be an example of a bio-information measuring method performed by the bio-information measuring apparatuses 100 and 200 according to the embodiments of FIGS. 1 and 2, which will be briefly described below to avoid redundancy.

The bio-information measuring apparatus 100, 200 may receive a request for measuring bio-information in operation 710. The request for measuring bio-information may be input from a user or an external device which communicates with the bio-information measuring apparatus 100, 200. However, the request for measuring bio-information is not limited thereto, and it may be determined automatically at predetermined intervals that the request for measuring bio-information is received. Upon receiving the request for measuring bio-information, the bio-information estimating apparatus may provide a user with guidance information on contact pressure to be applied by the user.

The bio-information measuring apparatus 100, 200 may control the pulse wave sensor to detect multi-wavelength pulse wave signals from an object in operation 720. In particular, the multiple wavelengths may include an infrared wavelength, a green wavelength, a red wavelength, a blue wavelength, and the like, but are not limited thereto. The pulse wave sensor may include one or more light sources to emit light of multiple wavelengths. For example, the pulse wave sensor may include a single light source configured to emit light of multiple wavelengths; or a plurality of light sources, each configured to emit light of different wavelengths. Further, the pulse wave sensor may include one or more detectors.

Upon detecting the multi-wavelength pulse wave signals in operation 720, the bio-information measuring apparatus 100, 200 may obtain a conversion signal based on the detected multi-wavelength pulse wave signals in operation 730. For example, the bio-information measuring apparatus 100, 200 may obtain the conversion signal, which indicates contact pressure between the pulse wave sensor and the object, by combining two or more pulse wave signals among the detected multi-wavelength pulse wave signals. For example, the bio-information measuring apparatus 100, 200 may generate a pulse wave DC signal of each wavelength by passing the multi-wavelength pulse wave signals through a low-pass filter (LPF), and may obtain the conversion signal by combining the generated two or more pulse wave DC signals of each wavelength. In particular, the bio-information measuring apparatus 100, 200 may generate differential signals by subtracting the pulse wave DC signal having the blue wavelength from the pulse wave DC signals having wavelengths other than the blue wavelength, and may obtain the conversion signal based on a ratio of the generated differential signals.

The bio-information measuring apparatus 100, 200 may obtain an oscillometric envelope based on the multi-wavelength pulse wave signals and the obtained conversion signal in operation 740. For example, the bio-information measuring apparatus 100, 200 may perform secondary differentiation on the pulse wave signals, and may extract a peak-to-peak amplitude, using a waveform envelope of the differentiated signal, by subtracting an amplitude value of a negative (−) point from an amplitude value of a positive (+) point of a waveform of the differentiated signal at each measurement time, and may obtain the oscillometric envelope by plotting the peak-to-peak amplitude with respect to a contact pressure value.

Then, the bio-information measuring apparatus 100, 200 may measure bio-information based on the obtained oscillometric envelope in operation 750. For example, the bio-information measuring apparatus 100, 200 may extract one or more features from the oscillometric envelope, and may measure bio-information, such as blood pressure, by using the extracted features. The bio-information measuring apparatus 100, 200 may extract, as the feature values, an amplitude value or a contact pressure value of a maximum peak of the oscillometric envelope, contact pressure values located to the left and right of the contact pressure value of the maximum peak and having a predetermined ratio (e.g., 0.5 to 0.7) to the contact pressure value of the maximum peak, and the like. The bio-information measuring apparatus 100, 200 may measure bio-information, such as blood pressure, by using the extracted feature values.

Subsequently, the bio-information measuring apparatus 100, 200 may output a measurement result of bio-information in operation 760. For example, the bio-information measuring apparatus 100, 200 may visually provide a user with the measurement result of bio-information, the extracted contact pressure value information, and the like through a display. Alternatively, the bio-information measuring apparatus 100, 200 may provide a user with warning information in a non-visual manner through voice, vibrations, tactile sensation, and the like.

Figure 8:
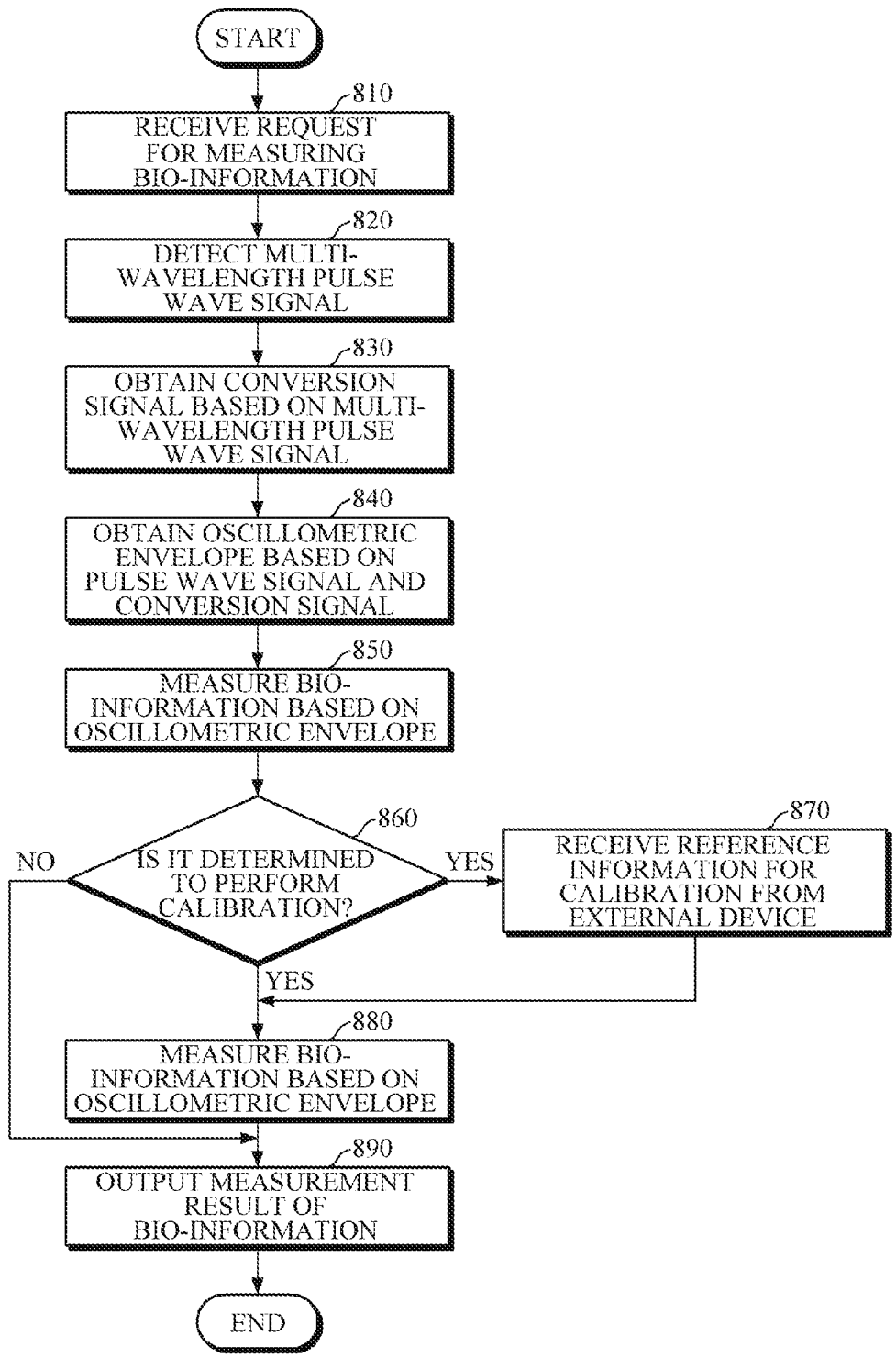
FIG. 8 is a flowchart illustrating a method of measuring bio-information according to another embodiment of the present disclosure.

FIG. 8 is a flowchart illustrating a method of measuring bio-information according to another embodiment of the present disclosure.

The method of FIG. 8 may be an example of a bio-information measuring method performed by the bio-information measuring apparatus 200 of FIG. 2.

Upon receiving a request for measuring bio-information in operation 810, the bio-information measuring apparatus 200 may control the pulse wave sensor to detect multi-wavelength pulse wave signals from an object in operation 820. In this case, the multiple wavelengths may include an infrared wavelength, a green wavelength, a red wavelength, a blue wavelength, and the like, and the pulse wave sensor may include one or more light sources to emit light of multiple wavelengths.

Then, upon detecting the multi-wavelength pulse wave signals in operation 820, the bio-information measuring apparatus 200 may obtain a conversion signal based on the detected multi-wavelength pulse wave signals in operation 830. For example, the bio-information measuring apparatus 200 may generate pulse wave DC signals by filtering the multi-wavelength pulse wave signals, and may obtain the conversion signal by combining the generated two or more pulse wave DC signals.

Subsequently, the bio-information measuring apparatus 200 may obtain an oscillometric envelope based on the multi-wavelength pulse wave signals and the obtained conversion signal in operation 840, and may measure bio-information based on the obtained oscillometric envelope in operation 850. For ample, the bio-information measuring apparatus 200 may extract one or more features from the oscillometric envelope, and may measure bio-information, such as blood pressure, by using the extracted features.

Next, the bio-information measuring apparatus 200 may determine whether to calibrate the measured bio-information value in operation 860. For example, the bio-information measuring apparatus 200 may determine whether to calibrate the measured bio-information value based on predetermined criteria for determining calibration, which are obtained using one, or a combination of two or more of, a normal range of bio-information measurement values, a number of times the information measurement values continuously fall outside a normal range, a total number of times the bio-information measurement values fall outside a normal range during a predetermined period of time, an object's state change, a user's health condition, and the like.

Then, upon determining to perform calibration in operation 860, the bio-information measuring apparatus 200 may calibrate bio-information based on reference information for calibration in operation 880. In this case, in response to the predetermined criteria being satisfied, the bio-information measuring apparatus 200 may communicate with an external device before performing calibration, to receive the reference information for calibration from the external device in operation 870, and may calibrate the bio-information measurement value by using the received reference information in operation 880.

By contrast, upon determining in operation 860 that calibration is not required, the bio-information measuring apparatus 200 may output the bio-information measurement value measured in operation 850, or the calibrated bio-information measurement value in operation 890.

Figure 9:
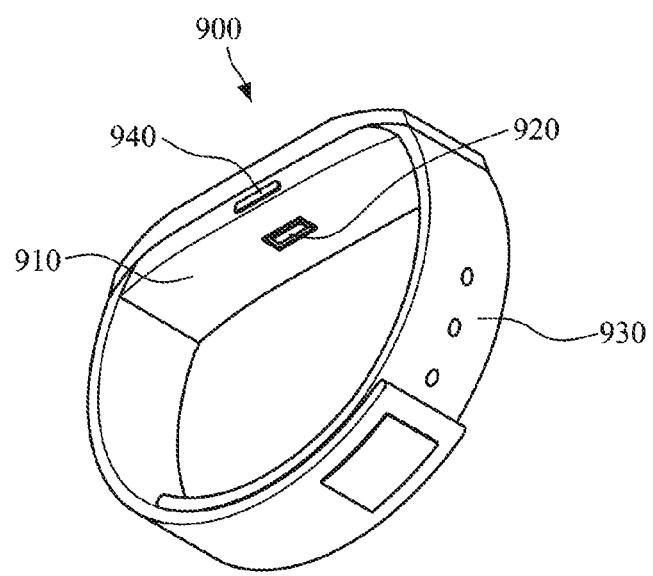
FIG. 9 is a diagram illustrating a wearable device, to which an apparatus for measuring bio-information is applied.

FIG. 9 is a diagram illustrating a wearable device, to which an apparatus for measuring bio-information is applied. Various embodiments of the apparatus for measuring bio-information described above may be mounted in a smart watch worn on a wrist or a smart band-type wearable device as illustrated in FIG. 9. However, the wearable device is merely an example for convenience of explanation, and it should not be construed that application of the embodiments is limited to a smart watch or a smart band-type wearable device.

Referring to FIG. 9, the wearable device 900 includes a main body 910 and a strap 930.

The strap 930 may be flexible, and may be connected to both ends of the main body 910 to be bent around a user's wrist or may be bent in a manner which allows the strap 930 to be detached from a user's wrist. Alternatively, the strap 930 may be formed as a band that is not detachable. In this case, air may be injected into the strap 930 or an airbag may be included in the strap 930, so that the strap 930 may have elasticity according to a change in pressure applied to the wrist, and the change in pressure of the wrist may be transmitted to the main body 910.

A battery, which supplies power to the wearable device 900, may be embedded in the main body 910 or the strap 930.

Further, the wearable device 900 may include a pulse wave sensor 920 which measures a pulse wave signal and a contact pressure signal from an object; and a processor 120 which measures a user's bio-information by using the pulse wave signal and the contact pressure signal which are measured by the pulse wave sensor 920.

The pulse wave sensor 920 may be mounted at a bottom portion of the main body 910, i.e., a portion that is exposed to come into contact with an object (e.g., a user's wrist), to measure a pulse wave signal from the object. The pulse wave sensor 920 may include one or more light sources which emit light onto an object. In particular, each of the light sources may emit light of different wavelengths. Further, the pulse wave sensor 920 may include one or more detectors which detect light emanating from the object. The one or more light sources may be positioned at different distances from the detectors.

In response to a user's request for measuring bio-information, the processor 120 may generate a control signal to control the pulse wave sensor 920, and may obtain a conversion signal, which indicates contact pressure, by using multi-wavelength pulse wave signals measured by the pulse wave sensor 920.

The processor 120 may obtain an oscillometric envelope by using the multi-wavelength pulse wave signals and the conversion signal, and may measure bio-information, such as blood pressure, based on the obtained oscillometric envelope, which is described above such that detailed description thereof will be omitted.

Upon receiving the request for measuring bio-information from a user, the processor 120 may provide guidance information on contact pressure to the user through a display, so that the user may apply pressure to the main body 910 to change contact pressure between the pulse wave sensor 920 and the object.

The display may be mounted on a front surface of the main body 910, and may visually output guidance information on contact pressure and/or a measurement result of bio-information.

The processor 120 may manage, in a storage device, a measurement result of bio-information, for example, such as a measured blood pressure value, blood pressure history information, the pulse wave signal and the contact pressure signal which are used to measure each blood pressure value, and various types of information including extracted features and the like. Further, the processor 120 may further generate information, such as alarm or warning information associated with a measured bio-information value, a health condition change trend, and the like, which are required in order to provide health care to a user, and my manage the generated information in a storage device.

Further, the wearable device 900 may include a manipulator 940 which receives a control command of a user and transmits the received control command to the processor 120. The manipulator 940 may be mounted on a side surface of the main body 910, and may include a function for inputting a command to turn on/off the wearable device 900.

Moreover, the wearable device 900 may include a communication interface 230 for transmitting and receiving various data to and from an external device 250, and various other modules for performing additional functions provided by the wearable device 900.

Figure 10A:
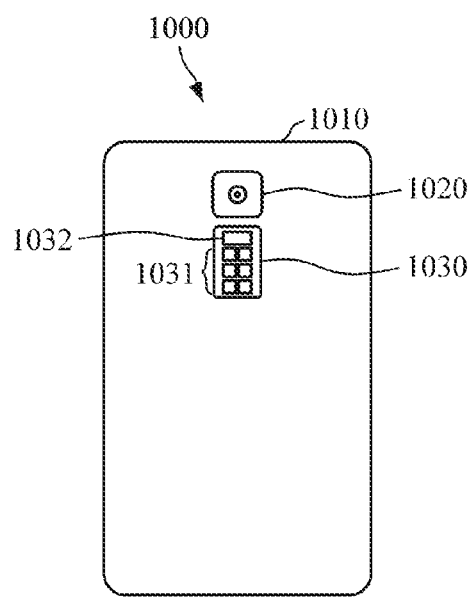
FIGS. 10A and 10B are diagrams illustrating a smart device, to which an apparatus for measuring bio-information is applied.
Figure 10B:
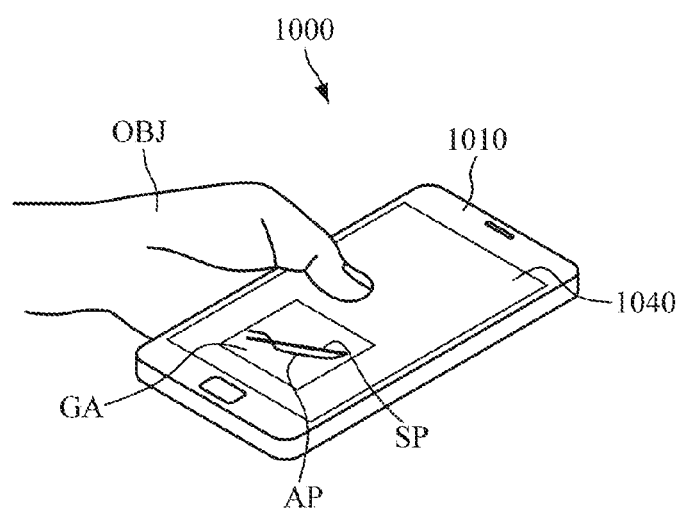

FIGS. 10A and 10B are diagrams illustrating a smart device, to which an apparatus for measuring bio-information is applied.

FIGS. 10A and 10B are diagrams illustrating a smart device, to which embodiments of an apparatus for measuring bio-information are applied. Examples of the smart device may include a smartphone, a tablet PC, and the like.

Referring to FIGS. 10A and 10B, the smart device 1000 includes a main body 1010 and a pulse wave sensor 1030 mounted on a rear surface of the main body 1010 to be exposed to the outside. In this case, the pulse wave sensor 1030 may include one or more light sources 1031 and one or more detectors 1032. Each of the light sources 1031 may include a light emitting diode (LED) and the like, and at least some of the light sources 1031 may be configured to emit light of different wavelengths. Each of the detector 1032 may include a photo diode, a photo transistor, and the like.

In addition, a display 1040 may be mounted on a front surface of the main body 1010. The display 1040 may visually output guidance information on contact pressure, a measurement result of bio-information, and the like.

For example, when a user touches the pulse wave sensor 1030 with an object OBJ to measure bio-information, the display 1040 may output an identification mark SP, which indicates a reference contact pressure to be applied by the user's object OBJ while a pulse wave signal is measured, on a predetermined area GA.

Further, once the processor 120 obtains a conversion signal which indicates contact pressure, by using multi-wavelength pulse wave signals, the display 1040 may output an identification mark AP which indicates contact pressure at each measurement time. In this case, the display 1040 may display, in different colors and the like, the reference contact pressure and the contact pressure obtained based on the conversion signal, so that a user may easily distinguish the reference contact pressure and the contact pressure. In addition, once the processor 120 determines that a contact state is not normal by comparing the reference contact pressure at each measurement time with the contact pressure obtained based on the conversion signal, the display 1040 may output an identification mark which indicates the point at which the contact state is not normal, or may output a warning message for changing the contact state, and the like, but is not limited thereto.

Moreover, an image sensor 1020 may be mounted in the main body 1010. When an object (e.g., finger) approaches the pulse wave sensor 1030 to measure a pulse wave signal, the image sensor 1020 may capture an image of the finger and may transmit the captured image to the processor 120. In this case, based on the image of the finger, the processor 120 may identify a relative position of the finger with respect to an actual position of the pulse wave sensor 1030, and may provide the relative position of the finger to the user through the display 1040 so that pulse wave signals may be measured with improved accuracy.

Various other modules for performing many embodiments of the apparatus for measuring bio-information described above may be mounted in the smart device 1000, and detailed description thereof will be omitted.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for measuring bio-information, the apparatus comprising:
   a pulse wave sensor configured to emit light of multiple wavelengths onto an object, and detect the light to obtain multi-wavelength pulse wave signals when the light is reflected or scattered from the object; and
   a processor configured to:
   obtain a conversion signal that estimates a contact pressure between the object and the pulse wave sensor, based on differences between the multi-wavelength pulse wave signals, without using a force sensor or a pressure sensor to measure the contact pressure,
   obtain an oscillometric envelope based on the multi-wavelength pulse wave signals and the conversion signal, and
   obtain bio-information based on the oscillometric envelope,
   wherein the bio-information comprises at least one of a blood pressure, a vascular age, an arterial stiffness, an aortic pressure waveform, a vascular compliance, a stress index, and a degree of fatigue.

2. The apparatus of claim 1, wherein the pulse wave sensor comprises:
   one or more light sources configured to emit the light of the multiple wavelengths onto the object; and
   one or more detectors configured to detect the light of the multiple wavelengths when the light is reflected or scattered from the object.

3. The apparatus of claim 1, wherein the multi-wavelength pulse wave signals comprise a first pulse wave signal having a first wavelength, a second pulse wave signal having a second wavelength, and a third pulse wave signal having a third wavelength, and
   wherein the processor is further configured to:
   obtain a first differential signal representing a difference between the first pulse wave signal and the second pulse wave signal, and a second differential signal representing a difference between the second pulse wave signal and the third pulse wave signal; and
   obtain the conversion signal that estimates the contact pressure between the object and the pulse wave sensor, based on a ratio between the first differential signal and the second differential signal.

4. The apparatus of claim 1, wherein the processor is further configured to obtain a differential signal between the multi-wavelength pulse wave signals, and obtain the conversion signal based on the differential signal.

5. The apparatus of claim 4, wherein the processor is further configured to obtain the conversion signal corresponding to the differential signal, based on a correlation model that uses a correlation between an intensity of the differential signal at each measurement time and an actual contact pressure.

6. The apparatus of claim 4, wherein the multi-wavelength pulse wave signals comprise a pulse wave signal having a blue wavelength, and
   the processor is further configured to obtain the differential signal by subtracting the pulse wave signal having the blue wavelength from the pulse wave signals having wavelengths other than the blue wavelength.

7. The apparatus of claim 1 wherein the multi-wavelength pulse wave signals comprise a pulse wave signal having a blue wavelength, a pulse wave signal having a green wavelength, and a pulse wave signal having a red wavelength, and the processor is further configured to obtain a first differential signal by subtracting the pulse wave signal having the blue wavelength from the pulse wave signal having the green wavelength, a second differential signal obtained by subtracting the pulse wave signal having the blue wavelength from the pulse wave signal of the red wavelength, and obtain the conversion signal based on a ratio between the first differential signal and the second differential signal.

8. The apparatus of claim 1, wherein the processor is further configured to:

select one or more pulse wave signals from the multi-wavelength pulse wave signals based on at least one of a maximum amplitude value of each of the multi-wavelength pulse wave signals, an average amplitude value of each of the multi-wavelength pulse wave signals, and a difference between the maximum amplitude value and a minimum amplitude value of each of the multi-wavelength pulse wave signals, and obtain the oscillometric envelope based on the selected one or more pulse wave signals and the conversion signal.

9. The apparatus of claim 1, wherein the processor is further configured to:

select, from the multi-wavelength pulse wave signals, a first pulse wave signal and a second pulse wave signal that has a longer wavelength that the first pulse wave signal, obtain a differential signal by subtracting the first pulse wave signal from the second pulse wave signal, and obtain the oscillometric envelope based on the differential signal and the conversion signal.

10. The apparatus of claim 1, wherein the processor is further configured to:

select a plurality of pulse wave signals from the multi-wavelength pulse wave signals, obtain the oscillometric envelope using each of the selected pulse wave signals and the conversion signal, and obtain a combined oscillometric envelope by combining the oscillometric envelope obtained from each of the selected pulse wave signals.

11. The apparatus of claim 1, wherein the processor is further configured to:

select pulse wave signals from the multi-wavelength pulse wave signals, extract a peak-to-peak amplitude at each measurement time of the selected pulse wave signals, and obtain the oscillometric envelope by plotting the extracted peak-to-peak amplitude with respect to a value of the conversion signal corresponding to the each measurement time.

12. The apparatus of claim 1, wherein the processor is further configured to extract as features at least one of an amplitude value of a maximum peak of the oscillometric envelope, a contact pressure value of the maximum peak of the oscillometric envelope, and contact pressure values located having a predetermined ratio to the contact pressure value of the maximum peak.

13. The apparatus of claim 1, further comprising a display configured to, based on receiving a request for measuring bio-information, display information on a reference contact pressure to be applied by a user to the pulse wave sensor.

14. The apparatus of claim 1, further comprising a display configured to display information on a measured contact pressure, applied by a user to the pulse wave sensor, based on the conversion signal.

15. A method of measuring bio-information, the method comprising:

emitting, by a pulse wave sensor, light of multiple wavelengths onto an object;

detecting, by the pulse wave sensor, the light to obtain multi-wavelength pulse wave signals when the light is reflected or scattered from the object;

obtaining a conversion signal that estimates a contact pressure between the object and the pulse wave sensor, based on differences between the multi-wavelength pulse wave signals, without using a force sensor or a pressure sensor to measure the contact pressure;

obtaining an oscillometric envelope based on the multi-wavelength pulse wave signals and the conversion signal; and obtaining bio-information based on the oscillometric envelope, wherein the bio-information comprises at least one of a blood pressure, a vascular age, an arterial stiffness, an aortic pressure waveform, a vascular compliance, a stress index, and a degree of fatigue.

16. The method of claim 15, wherein the multi-wavelength pulse wave signals comprise a first pulse wave signal having a first wavelength, a second pulse wave signal having a second wavelength, and a third pulse wave signal having a third wavelength, and wherein the obtaining the conversion signal comprises:

obtaining a first differential signal representing a difference between the first pulse wave signal and the second pulse wave signal, and a second differential signal representing a difference between the second pulse wave signal and the third pulse wave signal; and obtaining the conversion signal that estimates the contact pressure between the object and the pulse wave sensor, based on a ratio between the first differential signal and the second differential signal.

17. The method of claim 16, wherein the first wavelength, the second wavelength, and the third wavelength correspond to a green wavelength, a blue wavelength, and a red wavelength, respectively.

18. The method of claim 15, wherein the obtaining the conversion signal comprises:

based on the multi-wavelength pulse wave signals comprising a pulse wave signal having a blue wavelength, a pulse wave signal having a green wavelength, and a pulse wave signal having a red wavelength, obtaining a first differential signal by subtracting the pulse wave signal having the blue wavelength from the pulse wave signal having the green wavelength, and a second differential signal by subtracting the pulse wave signal having the blue wavelength from the pulse wave signal of the red wavelength; and obtaining the conversion signal based on a ratio between the first differential signal and the second differential signal.

19. The method of claim 15, wherein the obtaining the oscillometric envelope comprises:

selecting one or more pulse wave signals from the multi-wavelength pulse wave signals based on at least one of a maximum amplitude value of each of the multi-wavelength pulse wave signals, an average amplitude value of each of the multi-wavelength pulse wave signals, and a difference between the maximum amplitude value and a minimum amplitude value of each of the multi-wavelength pulse wave signals; and obtaining the oscillometric envelope based on the selected one or more pulse wave signals and the conversion signal.

20. The method of claim 15, wherein the obtaining the oscillometric envelope comprises:

selecting, from the multi-wavelength pulse wave signals, a first pulse wave signal and a second pulse wave signal that has a longer wavelength than the first pulse wave signal;

obtaining a differential signal by subtracting the first pulse wave signal from the second pulse wave signal; and obtaining the oscillometric envelope based on the differential signal and the conversion signal.

21. The method of claim 15, wherein the obtaining the oscillometric envelope comprises:

selecting a plurality of pulse wave signals from the multi-wavelength pulse wave signals;

obtaining the oscillometric envelope using each of the selected pulse wave signals and the conversion signal; and obtaining a combined oscillometric envelope by combining the oscillometric envelope obtained from each of the selected pulse wave signals.

22. The method of claim 15, wherein the obtaining the bio-information comprises extracting as features at least one of an amplitude value of a maximum peak of the oscillometric envelope, a contact pressure value of the maximum peak of the oscillometric envelope, and contact pressure values located having a predetermined ratio to the contact pressure value of the maximum peak.

* * * * *